(12) United States Patent
Hwang et al.

(10) Patent No.: US 11,292,944 B2
(45) Date of Patent: Apr. 5, 2022

(54) ADHESIVE COMPOSITION AND METHOD FOR PREPARING SAME

(71) Applicant: CJ CHEILJEDANG CORPORATION, Seoul (KR)

(72) Inventors: Ji Ho Hwang, Seoul (KR); Jun Ok Moon, Suji-gu Yongin-si (KR); Young Lyeol Yang, Seoul (KR); Chang Suk Lee, Suji-gu Yongin-si (KR); Sang Gwon Moon, Seoul (KR); Su Jin Choi, Daegu (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 81 days.

(21) Appl. No.: 16/496,613

(22) PCT Filed: Mar. 21, 2018

(86) PCT No.: PCT/KR2018/003312
§ 371 (c)(1),
(2) Date: Sep. 23, 2019

(87) PCT Pub. No.: WO2018/174570
PCT Pub. Date: Sep. 27, 2018

(65) Prior Publication Data
US 2020/0017729 A1      Jan. 16, 2020

(30) Foreign Application Priority Data

Mar. 21, 2017  (KR) .................. 10-2017-0035512
Oct. 20, 2017  (KR) .................. 10-2017-0136615

(51) Int. Cl.
*C09J 11/06*   (2006.01)
*C09J 4/00*    (2006.01)

(52) U.S. Cl.
CPC .................. *C09J 11/06* (2013.01); *C09J 4/00* (2013.01)

(58) Field of Classification Search
None
See application file for complete search history.

(56) References Cited

U.S. PATENT DOCUMENTS

| | | |
|---|---|---|
| 4,959,412 A | 9/1990 | Arter et al. |
| 5,026,821 A | 6/1991 | Boustta et al. |
| (Continued) | | |

FOREIGN PATENT DOCUMENTS

| | | |
|---|---|---|
| CA | 1278132 C | 12/1990 |
| CN | 1210551 A | 3/1999 |
| (Continued) | | |

OTHER PUBLICATIONS

WO-2006001345-A1—English translation (Year: 2006).*
(Continued)

*Primary Examiner* — Stefanie J Cohen
(74) *Attorney, Agent, or Firm* — Cantor Colburn LLP (57) ABSTRACT

Provided is an adhesive composition including lysine, citric acid, and water, wherein the lysine and the citric acid are present in the form of an aqueous solution of a salt such that precipitates are not formed in the aqueous solution. In addition, provided is a method of preparing an adhesive composition including mixing lysine, citric acid, and water to thereby form a mixture of the lysine, the citric acid, and the water, and stirring the mixture at a temperature of 80° C. or less, wherein amounts of the lysine, the citric acid, and the water are adjusted such that precipitates of the lysine and the citric acid do not form in the adhesive composition.

10 Claims, 3 Drawing Sheets

(56) References Cited

U.S. PATENT DOCUMENTS

| | | | |
|---|---|---|---|
| 5,284,891 A | 2/1994 | Wouters et al. | |
| 6,166,102 A | 12/2000 | Ahn et al. | |
| 6,486,285 B2 | 11/2002 | Fujita | |
| 6,777,465 B2 | 8/2004 | Haile | |
| 7,306,844 B2 | 12/2007 | Chu et al. | |
| 7,939,145 B2 | 5/2011 | Dronzek, Jr. | |
| 8,519,031 B2 | 8/2013 | Parker et al. | |
| 2003/0064178 A1 | 4/2003 | Smith et al. | |
| 2008/0319101 A1* | 12/2008 | Nakajima | A61L 24/043 523/111 |

FOREIGN PATENT DOCUMENTS

| | | | |
|---|---|---|---|
| CN | 001334714 A | 2/2002 | |
| CN | 101475790 A | 7/2009 | |
| CN | 102190589 A | 9/2011 | |
| CN | 102329582 B | 1/2012 | |
| CN | 104379139 A | 2/2015 | |
| CN | 104583333 A | 4/2015 | |
| EP | 1310174 A1 | 5/2003 | |
| EP | 1849486 B1 | 4/2015 | |
| EP | 3299400 B1 | 6/2019 | |
| FR | 1458094 | 3/1966 | |
| FR | 1458094 A * | 3/1966 | |
| FR | 2648044 A1 | 12/1990 | |
| JP | 2002138161 A | 5/2002 | |
| JP | 2004002092 A | 1/2004 | |
| JP | 2007161642 A | 6/2007 | |
| JP | 4796493 B2 | 8/2011 | |
| JP | 59598867 B2 | 2/2013 | |
| JP | 2015117347 A | 6/2015 | |
| KR | 1020030018443 B1 | 6/2003 | |
| KR | 100401453 B1 | 10/2003 | |
| KR | 10989942 B1 | 10/2010 | |
| KR | 1020130086919 B1 | 5/2013 | |
| KR | 101427207 B1 | 8/2014 | |
| KR | 1020150023758 B1 | 3/2015 | |
| KR | 20160095132 A | 8/2016 | |
| RU | 2558365 C2 | 3/2010 | |
| WO | 1997019141 A1 | 5/1997 | |
| WO | 2006001345 A1 | 1/2006 | |
| WO | WO-2006001345 A1 * | 1/2006 | A61P 3/02 |
| WO | 2006012615 A2 | 2/2006 | |
| WO | 2007120653 A1 | 10/2007 | |
| WO | 2010071298 A2 | 6/2010 | |
| WO | 2011136568 A2 | 11/2011 | |
| WO | 2015086545 A1 | 6/2015 | |
| WO | 2015177114 A1 | 11/2015 | |

OTHER PUBLICATIONS

FR-1458094-A—English translation (Year: 1964).*
Acceptance decision with search report dated Mar. 25, 2020 in Russian Patent Application No. 2019131399/05, 9 pp.
English Abstract of JP 2002138161.
English translation of Acceptance decision with search report dated Mar. 25, 2020 in Russian Patent Application No. 2019131399/05, 4 pp.
Examination report dated Apr. 30, 2020 of Australian patent application No. 2018238179, which corresponds to the above-identified patent application.
Extended European Search Report dated Dec. 10, 2020 of the European Application No. 18770654, which corresponds to the above-identified application.
Search Report (English Translation) issued in PCT/KR2018/003314, dated Sep. 27, 2018, 2 pp.
Office Action dated May 14, 2019, issued in CN 201880000716.8, with English translation, 15 pp.
Office Action issued in TW Application No. 10720988390, dated Oct. 23, 2018, with Englsih translation, 11 pp.
Search Report (English Translation) issued in PCT/KR2018/003312, dated Jun. 28, 2018, 2 pp.
Acceptance decision with search report dated Mar. 24, 2020 of Russian patent application No. 2019131437/05, which corresponds to the above-identified patent application.
English translation of Acceptance decision with search report dated Mar. 24, 2020 of Russian patent application No. 2019131437/05, which corresponds to the above-identified patent application.
English translation of Patent Search Report issued in PCT/KR2018/003312 dated Mar. 24, 2020.
CAS Registry No. 61839-17-6; STN Entry Date Nov. 16, 1984; L-Lysine, compounds, methylenebutanedioate (1:1). Retrieved on Apr. 15, 2020.

* cited by examiner

ADHESIVE COMPOSITION AND METHOD FOR PREPARING SAME

CROSS REFERENCE TO RELATED APPLICATION

This application claims priority to PCT/KR2018/003312, filed on Mar. 21, 2018, which claims priority to Korean Application No. 10-2017-0035512, filed on Mar. 21, 2017, and Korean Application No. 10-2017-0136615, filed on Oct. 20, 2017, and all the benefits accruing therefrom under 35 U.S.C. § 371, the contents of which in their entirety are herein incorporated by reference.

BACKGROUND

1. Field

One or more embodiments relate to an adhesive composition and a method of preparing the same.

2. Description of the Related Art

In general, adhesives include a petroleum-derived monomer and an oil-based solvent as raw materials. Monomers made from petroleum-derived raw materials and adhesives made from such monomers may have problems such as decreases in production due to limited oil reserves, generation of endocrine-disrupting chemicals during production of the monomers and adhesives, and toxicity caused by disposal of the monomers and adhesives. In particular, since organic solvents derived from petroleum are used during manufacturing processes of conventional adhesives in order to improve the adhesive strength of the manufactured adhesives, the health of workers is threatened and there is growing concern about environmental pollution. In addition, since most of the adhesives include monomer units covalently bonded to each other, natural decomposition of the adhesives is difficult and undecomposed polymers may cause environmental pollution. Therefore, for the efficient removal of adhesives from adherends, various water-removable adhesives have been developed. In order to efficiently remove conventional water-removable adhesives from adherends and substrates, high-temperature and alkaline conditions are required, and additional energy needs to be consumed. In addition, secondary environmental pollution may be caused by the disposal of raw material molecules of the adhesives when the adhesives attached to adherends or substrates are removed by water.

SUMMARY

An aspect provides an adhesive composition.

Another aspect provides a method of preparing the adhesive composition.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, an adhesive composition according to an embodiment and a method of preparing the same will be described in detail.

An adhesive composition including lysine, citric acid, and water, wherein the lysine and citric acid are present in the form of an aqueous solution of a salt and do not form precipitates in the aqueous solution is provided.

Throughout the specification, the term "adhesion" refers to a phenomenon in which two objects (except for gases) are close to each other and a force (or work) is required to separate the two objects by pulling thereafter. If required, some materials having adhesion may be solidified after a given period of time after being applied to a substrate. When such an adhesive is separated from the substrate, irreversible physical destruction may occur. In addition, the term "adhesion" may include "viscoelasticity" which requires a force on viscoelastic deformation when the adhesive material is separated from the substrate. An adhesive composition having viscoelastic properties may be stored and distributed after pretreatment before being applied to the substrate. Thus, adhesive forces thereof may be maintained after a certain period of time. Examples of adhesive articles prepared by applying the adhesive composition to a substrate and drying the composition may include labels and oriented polypropylene (OPP) tapes. By using the adhesive properties, reversible attachment and detachment may be possible. By applying the adhesive composition to the substrate and drying the composition, an adhesive layer having viscoelasticity is formed on the substrate.

Meanwhile, viscosity refers to a property of inhibiting a flow of a substance caused by internal friction between molecules. In this case, friction is a force to prevent a difference in the distribution of flow velocities. Adhesion and viscosity are independent properties. A composition having a high viscosity may have a very low adhesion and a composition having a low viscosity may have a high adhesion.

Throughout the specification, the precipitates may include a water-insoluble salt AB(s) obtained by a chemical change of an aqueous solution of lysine A(aq) and an aqueous solution of itaconic acid B(aq) as shown in Reaction Scheme 1 below, a solid of lysine or itaconic acid A(s) precipitated from an aqueous solution of lysine or itaconic acid A(aq) as shown in Reaction Scheme 2 below, and a solid of lysine or itaconic acid A(s) not dissolved in a solvent but remaining in an insoluble state.

Reaction Scheme 1

Reaction Scheme 2

Also, the "precipitates" used herein may refer to precipitates formed selected from before the adhesive composition being applied to the substrate or adherend, during storage of the adhesive composition, and distribution of the adhesive composition.

As used herein, the term "lysine" refers to a basic α-amino acid and lysine may be biosynthesized from oxaloacetic acid via a lysine biosynthetic pathway or chemically synthesized.

Lysine may include one type of lysine or a mixture of at least two types of lysine.

Lysine may include at least one of L-lysine represented by Formula 1 below, D-lysine represented by Formula 2 below, and salts thereof.

Formula 1

Formula 2

The lysine salts may include, for example, lysine sulfate, lysine acetate, lysine monohydrochloride, lysine dihydrochloride, lysine monohydrate, lysine acetylsalicylate, lysine phosphate, lysine diphosphate, a mixture thereof, or a combination thereof. These lysine salts may be converted into lysine free forms.

Methods of converting lysine salts into lysine free forms are well known in the art. Also, commercially available lysine raw materials may be used. For example, the lysine may be D-lysine, L-lysine, and/or DL-lysine. Since physicochemical properties thereof are the same or similar, characteristics of adhesive compositions including the same are also the same or similar, and thus they may be included in the scope of the present disclosure.

Citric acid is an organic acid represented by Formula 3 below.

Formula 3

In the adhesive composition, lysine and citric acid may be present in the form of an aqueous solution of a salt. Specifically, although lysine, citric acid, and water are mixed, lysine and citric acid may be present in the form of an aqueous solution of a salt without forming a covalent compound or an insoluble salt.

In the adhesive composition according to an embodiment, the contents of lysine, citric acid, and water may be adjusted such that lysine and citric acid are not precipitated into crystals or are formed into precipitates. When the adhesive composition is maintained in a liquid phase without forming crystals or precipitates, the adhesive composition may have excellent adhesion and may be uniformly applied to the substrate.

A mixing molar ratio of lysine to citric acid may be from 1.7:1 to 1:3. Particularly, the mixing molar ratio of lysine to citric acid may be from 1.7:1 to 1:2, 1.7:1 to 1:1.5, 1.5:1 to 1:1.5, or 1.5:1 to 1:1. When the content of lysine to that of citric acid is more than or less than the ranges described above, precipitates are formed in the composition, thereby decreasing adhesion or deteriorating storage stability or preservation stability.

A solid content of the adhesive composition may be equal to or less than 70 parts by weight, for example, from 0.1 to 70 parts by weight, from 1 to 70 parts by weight, or from 10 to 70 parts by weight, based on 100 parts by weight of the composition. When the solid content is within the ranges described above, the adhesive composition may be easily applied to the substrate. When the solid content is greater than 70 parts by weight, the composition cannot be used as an adhesive composition due to the formation of precipitates in the adhesive composition. Although the solid content decreases, the adhesive composition does not precipitate or lose the adhesive force. Thus, the solid content may be adjusted from 0.1 to 10 parts by weight in accordance with application fields.

Citric acid and lysine may be included in the adhesive composition as active ingredients. A sum of the contents of citric acid and lysine may be from 60 to 100 parts by weight, from 70 to 99 parts by weight, from 80 to 98 parts by weight, or from 85 to 97 parts by weight based on 100 parts by weight of the solid content of the adhesive composition.

According to another aspect, citric acid and lysine may be included in the form of a condensate including citric acid and lysine as a unit. For example, the condensate may be a dimer, a trimer, or an oligomer. The content of the condensate may be equal to or less than 20 parts by weight, equal to or less than 10 parts by weight, or equal to or less than 1 part by weight, or 0 part by weight based on 100 parts by weight of the sum of the contents of the citric acid and lysine. When the content of the condensate is higher than the ranges described above, the adhesive force of the adhesive composition may decrease or the adhesive composition may not be maintained in the liquid phase.

The effects of the adhesive composition according to an embodiment on adhesion as described above will be described as follows. These and other effects are not to be construed as being limited to those described below and may also be explained by other effects within the scope of no scientific contradiction.

Lysine has two amino groups and citric acid has three carbonyl groups. An unshared electron pair of oxygen of a carbonyl group of citric acid may interact with hydrogen of an amino group of lysine via an ionic hydrogen bond.

Thus, when components of the adhesive composition according to an embodiment are analyzed by liquid chromatography of the like, lysine and citric acid may be identified as raw materials. Thus, it may be confirmed that lysine and citric acid are bonded via an ionic hydrogen bond in the adhesive composition and are present in the form of an aqueous solution of a salt. In the adhesive composition according to an embodiment, lysine and citric acid may have excellent adhesive properties while being maintained in a liquid phase at room temperature (25° C.) without forming crystals (solid state) or precipitates.

The adhesive composition according to the present disclosure has water removability. Thus, when the adhesive composition according to the embodiment is used as an adhesive, the adhesive is dissociated from the substrate or adherend to which the adhesive is applied by water, and thereby easily separated and removed therefrom. Particularly, the adhesive applied to the substrate or adherend may be dissociated within 12 hours, particularly, within 6 hours, or more particularly, within 2 hours at room temperature (25° C.) by a stirring or washing process using water. The adhesive composition according to an embodiment is easily dissociated by water and dissociated components are also environmentally friendly since they are not harmful to living organisms and the environment.

The adhesive composition according to the present disclosure may further include at least one alcohol solvent selected from a primary alcohol, a polyhydric alcohol, a dial, and a triol. When a solvent is further added to the adhesive composition, a drying rate of the adhesive composition may be increased and processibilty of the adhesive composition may be improved.

A mixing weight ratio of deionized water to alcohol in the adhesive composition according to the embodiment may be from 1:1 to 10:0. More particularly, the mixing weight ratio of deionized water to alcohol in the adhesive composition may be from 1:1 to 10:1, from 1:1 to 5:1, or from 1:1 to 3:2. As the content of alcohol increases in the adhesive composition, the adhesive composition is more efficiently dried and has better coating, thereby increasing peel strength. However, when the content of alcohol is greater than 1.5 times or greater than that of deionized water in the adhesive composition, phase separation may occur in the adhesive composition.

The alcohol solvent may be a monohydric alcohol, a polyhydric alcohol, an unsaturated aliphatic alcohol, an alicyclic alcohol, or any mixture thereof. The monohydric alcohol may include at least one selected from methanol, ethanol, propane-2-ol, butane-1-ol, pentane-1ol, and hexadecane-1-ol. The polyhydric alcohol may include at least one selected from ethane-1,2-diol, propane-1,2-diol, propane-1,2,3-triol, butane-1,3-diol, butane-1,2,3,4-tetraol, pentane-1,2,3,4,5-pentol, hexane-1,2,3,4,5,6-hexol, and heptane-1,2,3,4,5,6,7-heptol.

The unsaturated aliphatic alcohol may include, for example, at least one selected from prop-2-ene-1-ol, 3,7-dimethylocta-2,6-dien-1-ol, prop-2-yn-1-ol, cyclohexane-1,2,3,4,5,6-hexol, and 2-(2-propyl)-5-methyl-cyclohexane-1-ol.

The pH of the adhesive composition may be from 2 to 11, particularly, from 2 to 9.5, more particularly, from 2 to 8.5. An adhesive composition having the pH within the ranges described above has excellent storage stability and preservation stability and may not change in formulation or quality even after a long term storage. The adhesive composition may have excellent adhesion without forming precipitates when used not only immediately after production but also after a long term storage.

Particularly, the adhesive composition may be a composition in which precipitates are not formed after being stored or distributed for 14 days or more. For example, since the adhesive composition is stable, physical properties thereof may be maintained after being stored for 14 days or more, for example, 12 months or more, for example, for 24 months or more. Also, a temperature of an environment in which the adhesive composition is stored may be from −18° C. to 80° C., particularly, −18° C. to 45° C., 0° C. to 60° C., or 20° C. to 40° C. Although the adhesive composition is stored in a temperature out of the temperature ranges above, formulation and quality of the adhesive composition may not be affected so long as a temperature of an environment in which the adhesive composition is used is within the ranges above. For example, when the adhesive composition is stored at a low temperature, the adhesive composition may be used after being maintained at room temperature for a predetermined time before use.

The adhesive composition according to the embodiment may have a contact angle of 15° to 70° when applied to the surface of the substrate.

The substrate may be any adherend commonly used in the art to which the adhesive composition is applicable. The substrate may be, for example, a glass substrate, a stainless steel (SUS) substrate, or a polymer film. As the polymer film, for example, a polyolefin film such as polyethylene, polypropylene, an ethylene/propylene copolymer, polybutene-1, an ethylene/vinyl acetate copolymer, a polyethylene/styrenebutadiene rubber mixture, or a polyvinylchloride film may be generally used. In addition, a plastic material such as polyethyleneterephthalate, polycarbonate, and poly (methylmethacrylate) or a thermoplastic elastomer such as polyurethane, and a polyamide-polyol copolymer, and any mixture thereof may also be used. When a glass substrate is used as the substrate, the adhesive composition may be more uniformly coated on glass having hydrophilicity, and thus a film forming property of the adhesive composition may be improved. When an SUS substrate used as the substrate, citric acid included in the adhesive composition induces interactions with the SUS, and thus adhesion between the substrate and an adhesive layer formed from the adhesive composition is improved. When glass or SUS is used as the substrate as described above, a contact angle of the adhesive composition with the substrate may decrease in comparison with a polyethylene film having hydrophobicity, and thus the adhesive composition may be more easily coated on the substrate.

As the solid content increases in the adhesive composition applied to the substrate described above, the contact angle of the adhesive composition with the substrate decreases. When the contact angle of the adhesive composition with the substrate decreases as described above, an adhesive layer may be uniformly formed by applying the adhesive composition to the substrate and drying the composition and may have improved adhesive force to the substrate. The contact angle may be measured by using a contact angle meter via a Sessile Drop method. The contact angle may be measured by using, for example, a product of Phoenix company (e.g.: Phoenix-150, Phoenix-MT, Phoenix-Alpha, Phoenix-Smart, Phoenix 300 Touch, or Phoenix-multi) with a drop volume of 5 μl.

A contact angle of an adhesive layer formed of the adhesive composition according to the present embodiment with the substrate may be from 15° to 70°. Specifically, a contact angle of the adhesive layer may decrease with a substrate having a higher surface energy. According to another embodiment, the contact angle of the adhesive layer with a glass substrate may be, for example, equal to or less than 20°, for example, from 15° to 20°. A contact angle of the adhesive layer with a SUS substrate and the adhesive layer may be, for example, from 40° to 70°, and a contact angle of the adhesive layer with a polyethylene film may be, for example, from 60° to 70°. According to another aspect of the present disclosure, a method of preparing the adhesive composition including mixing lysine, citric acid, and water and stirring the mixture at a temperature of 80° C. or less is provided.

When the mixing of lysine, citric acid, and water and stirring the mixture is performed at a temperature out of the above-described temperature range, side reaction products, impurities, and the like may be produced. In some cases, it may be difficult to obtain an adhesive composition having desired adhesion.

The stirring of the mixture at a temperature of 80° C. or less may be performed at a temperature of, for example, 0° C. to 80° C. More particularly, this step may be performed at a temperature of 0° C. to 75° C., 0° C. to 70° C., 0° C. to 65° C., or 0° C. to 60° C.

The stirring of the mixture at a temperature of 80° C. or less may include i) a first step of mixing and stirring at a temperature of, for example, 0° C. to 80° C., 0° C. to 75° C., 0° C. to 70° C., or 0° C. to 60° C. and ii) a second step of cooling to room temperature (20° C. to 30° C.).

The mixing of lysine, citric acid, and water may be performed by adding citric acid to an aqueous solution of lysine or by simultaneously mixing lysine, citric acid, and water.

The method may further include removing water and a solvent by concentration under reduced pressure to control the solid content of the adhesive composition to a predetermined range.

According to another aspect of the present disclosure, an adhesive product including the adhesive composition applied to the substrate is provided. The adhesive product may include a substrate and an adhesive layer obtained by applying the adhesive composition to the substrate and drying the adhesive composition. The solvent included in the composition may be removed by drying. The drying may be performed at a temperature of 25° C. to 45° C.

According to another aspect of the present disclosure, provided is a method of attaching a first substrate to a second substrate including: applying the adhesive composition to the first substrate to bond the adhesive composition to the first substrate; and brining the first substrate to which the adhesive composition is bonded into contact with the second substrate to attach the first substrate to the second substrate.

The first substrate and the second substrate may be each independently selected from glass, stainless steel, polymer film, metal, plastic, paper, fiber, and soil, without being limited thereto. For example, the first substrate may be formed of the same material as the second substrate.

The adhesive composition or the adhesive product according to an embodiment, as a water-removable adhesive, may be used as adhesive tapes, spray-type adhesives for labeling, dust removers, or the like and may be easily removed from an adherend by using water without damaging the adherend, and packing materials may be easily recycled. In addition, when the adhesive composition or adhesive product is applied to pesticides and seeds, an application range thereof may be widened due to water-removable properties thereof. The water-removable adhesive according to the present embodiment may be manufactured with lower costs, may be more easily handled, and may improve workability and cleanness of working environments in comparison with conventional organic solvent-type adhesives.

A bio-derived monomer may be selected as a starting material to prepare the adhesive composition according to the present embodiment. Since the bio-derived monomer may be used in living organisms, environmental pollutions caused by petroleum-derived monomers, polymers, or oligomers obtained by separating the adhesive using water may be prevented in advance. Structures such as adhesive tapes and sheets for labels produced by using the adhesive composition according to the present embodiment as a water-removable adhesive have improved mechanical strength such as tensile strength and peel strength.

According to another embodiment, the adhesive composition or adhesive product may further include at least one additive selected from a reactive diluent, an emulsifier, a tackifier, a plasticizer, a filler, an antiaging agent, a curing accelerator, a flame retardant, a coagulant, a surfactant, a thickener, an UV screening agent, an elastomer, a pigment, a dye, a flavoring agent, an antistatic agent, an antiblocking agent, a slip agent, an inorganic filler, a kneading agent, a stabilizer, a modifying resin, a coupling agent, a levelling agent, a fluorescent whitening agent, a dispersant, a thermal stabilizer a photostabilizer, an UV absorbent, a wax, a wetting agent, an antioxidant, a preservative, and a lubricant. Although a total amount of the additives is not particularly limited, and various additives may be included in various weight ranges according to field of application. The additives may be used in amounts commonly used in the art, respectively.

The reactive diluent is a diluent assisting each component of the composition to be uniformly applied to an article to which the composition is applied and including at least one selected from, for example, n-butylglycidylether, aliphaticglycidylether, 2-ethylhexylglycidylether, phenylglycidylether, o-cresylglycidylether, nonylphenylglycidylether, p-tertbutylphenylglycidylether, 1,4-butanedioldiglycidylether, 1,6-hexanedioldiglycidylether, neopentylglycidylether, 1,4-cyclohexanedimethyloldiglycidylether, polypropyleneglycoldiglycidylether, ethyleneglycoldiglycidylether, polyethyleneglycoldiglycidylether, diethyleneglycoldiglycidylether, resorcinoldiglycidylether, hydrogenated bisphenol-A glycidylether, trimethylolpropenetriglycidylether, glycerolpolyglycidylether, diglycerolpolyglycidylether, pentaerythritolpolyglycidylether, castor oil glycidylether, sorbitolpolyglycidylether, neodecanoic acid glycidylether, diglycidyl-1,2-cyclohexanedicarboxylate, diglycidyl-o-phthalate,N,N-diglycidylamine, N,N-diglycidyl-o-toluidine, triglycidyl-p-aminophenol, tetraglycidyldiaminodiphenylmethane, triglycidyl-isocyanate, 1,4-butanedioldiglycidylether, 1,6-hexanedioldiglycidylether, polypropyleneglycidyldiglycidylether, and triethylolpropenetriglycidylether.

For example, the emulsifier may include at least one selected from a copolymer of polyoxyethylene and polyoxypropylene, a copolymer of polyoxyethylene and polyoctylphenylether, and sodiumdodecylbenzenesulfide.

Examples of the tackifier may be rosin and modified products thereof (e.g.: rosin, hydrogenated rosin, polymerized rosin, maleated rosin, rosin glycerin, and rosin modified phenolic resin), a terpene-based resin (e.g.: a terpene resin, a terpene-phenol resin, a terpene-styrene resin, and a terpene-phenolic resin), a petroleum resin (e.g.: a C5 petroleum resin, a C9 resin, a bicyclic nonadiene petroleum resin, a hydrogenated petroleum resin, and a styrene-terpene resin), a phenolic resin, a polymethylstyrene resin, a ketonealdehyde resin, a xylene formaldehyde resin, a Cashew oil modified phenolic resin, a Tall oil modified phenolic resin, rubber, a resin emulsion (e.g.: a rosin emulsion, a TPR water based resin, a 2402 resin emulsion, and a petroleum resin emulsion), a coumarone indene resin, and the like.

The plasticizer may improve processing flow or elongation. The plasticizer may also improve functions of the composition, such as electric insulation, adhesion, cold resistance, light resistance, oil resistance, resistance to saponification, flame retardancy, thermal stability, easy processibilty (intramolecular activity), activity (intermolecular activity), and non-toxicity.

A plasticizer to improve cold resistance may include dioctyl adiphate (DOA), dioctyl azelate (DOZ), dioctyl sebacate (DOS), Flexol TOF (UCC company), polyethyleneglycolester, and the like. A plasticizer to improve heat resistance (non-volatility) and non-transmutation may include a polymer blend such as polyester and nitrile-butadiene rubber (NBR), trimellitic ester, and pentarythritol ester. A plasticizer to improve light resistance may include DOP, DOA, DOS, polyester, and epoxidized soybean oil (ESBO).

A plasticizer to improve oil resistance may include Phosflex aromatic phosphate ester (Product Name: TPP, TCP, 112 (CDP), and 179A (TXP)), polyester, NBR, and the like. A plasticizer to improve resistance to saponification may include TCP, ESBO, polyester, and the like.

A plasticizer to improve flame retardancy may include phosphate such as TCP and TXP, chlorinated paraffin, chlorinated alkylstearate, NBR, and the like. A plasticizer to improve thermal stability may include ESBO, DOZ, DOS, DOP, polyethyleneglycol ester, and the like.

A plasticizer to improve easy processibilty may include DOA, BBP, TOF, TCP, octyldiphenyl phosphate, and the like. A plasticizer to improve activity may include DOZ, DOS, dibasic lead phosphate (DLP), ESBO, polyethyleneglycolester, and the like.

A plasticizer for non-toxicity may include BPBG, octyldiphenylphosphate, ESBO, ester of citric acid, NBR, and the like.

More particularly, examples of the plasticizer may include dibutylphthalate (DBP), dihexylphthalate (DHP), di-2-ethylhexylphthalate (DOP), di-n-octylphthalate (DnOP), diisooctylphthalate (DIOP), didecylphthalate (DDP), diisodecylphthalate (DIDP), C8-C10 mixed higher alcohol phthalate, butylbenzyl phthalate (BBP), dioctyladipate (DOA), dioctylazelate (DOZ), dioctylsebacate (DOS), tricresyl phosphate (TCP), trixylenyl phosphate (TXP), monooctyldiphenylphosphate (Santicizer141), monobutyldixylenyl phosphate, trioctylphosphate (TOF), aromatic oil, polybutene, paraffin, and the like.

As used herein, the thickener may be, for example, alginin, alginic acid, sodium alginate, guar gum, xanthan gum, collagen, alginate, gelatin, Furcellaran, agar, carrageenan, casein, locust bean gum, pectin, polyethyleneoxide, polyethyleneglycol, polyvinylalcohol, and polyvinylpyrrolidone.

The surfactant may be any surfactant commonly used in the art. For example, the surfactant may include C8-C18 alkyl sulfate, alkyl ether sulfate or alkyl aryl ether sulfate having 8 to 18 carbon atoms, 40 or less of ethylene oxide or propylene oxide units, and a hydrophobic group, C8-C18 alkyl sulfonate, alkylaryl sulfonate, ester and semi-ester of sulfosuccinic acid including monohydric alcohol or alkylphenol, and alkyl polyglycol ether or alkyl aryl polyglycol ether having C8-C40 ethylene oxide units. For example, sodium dodecyl sulfate (SDS), sodium-silicate, and the like may be used therefor.

The filler is added to improve strength, durability, and workability of the composition. Examples of the filler may include calcium carbonate, talc, ceramic, silica, dolomite, clay, titanium white, flowers of zinc, carbon (preventing shrinkage or blocking), potassium carbonate, titanium oxide, liquid polysulfide polymer, volatile diluent, magnesium oxide, processing oil, and the like.

The curing accelerator may be, for example, dibutyltin dilaurate, JCS-50 (Johoku Chemical Company Ltd.), or Formate TK-1 (Mitsui Chemical Polyurethane Corporation). Te antiaging agent may be, for example, dibutyl hydroxy toluene (BHT), IRGANOX® 1010, IRGANOX® 1035FF, or IRGANOX® 565 (all manufactured by Chiba Specialty Chemicals).

The antistatic agent is not particularly limited and examples thereof may include 1-hexyl-4-methylpyridinium hexafluorophosphate, dodecylpyridinium hexafluorophosphate, a fluorinated organometallic compound (e.g., HQ-115 of 3M), an alkali metal salt (e.g., $NaPF_6$, $NaSbF_6$, $KPF_6$, and $KSbF_6$), a conductive polymer (e.g., polythiophene (PEDOT of Bayer), polyaniline, and polypyrrole), a metal oxide (e.g., indium-doped tin oxide (ITO), antimony-doped tin oxide (ATO), tin oxide, zinc oxide, antimony oxide, and indium oxide), a quaternary ammonium salt (e.g., poly(acrylamide-co-diallyldimethyl ammonium chloride) solution of Sigma-Aldrich), 1-butyl-3-methylimidazolium hexafluorophosphate [BMIM][$PF_6$], 1-butyl-3-(2-hydroxyethyl) imidazolium bis(trifluoromethane sulfonyl)imide [BHEIM][$NTf_2$], and tetrabutylmethylammonium bis(trifluoromethanesulfonyl)imide [TBMA][$NTf_2$] which may be used alone or in combination of at least two thereof.

The elastomer refers to a rubber or a polymer having properties of an elastomer and may be, for example, ethylene-vinylacetate copolymer, acrylic rubber, natural rubber, isoprene rubber, styrene butadiene rubber, chloroprene rubber, butyl rubber, ethylene propylene rubber, styrene-ethylene-butylene-styrene copolymer, or acrylonitrile-butadiene copolymer.

The stabilizer stabilizes the adhesive force of the adhesive composition or the like and examples thereof may include polyhydric alcohol, polyvalent amine, or the like. For example, at least one selected from alkylene glycol, dialkylene glycol, benzenediol, benzenetriol, dialcoholamine, trialcoholamine, arabitol, mannitol, isomalt, glycerol, xylitol, sorbitol, maltitol, erythritol, ribitol, dulcitol, lactitol, threitol, iditol, polyglycitol, alkylene diamine, alkenylene diamine, phenylene diamine, and n-aminoalkylalkane diamine may be used therefor.

The fluorescent whitening agent may be a benzooxazole compound, a benzothiazole compound, a benzoimidazole compound, or the like.

The pigment may be a natural pigment or a synthetic pigment or an inorganic pigment or an organic pigment classified by another criterion.

The flavoring agent may be, for example, but is not limited to, peppermint oil, spearmint oil, carvone, or menthol, used alone or in combination.

The flame retardant may be melamine cyanurate, magnesium hydroxide, agalmatolite, zeolite, sodium silicate, aluminum hydroxide, antimony (antimony trioxide), or the like. An additive to improve water resistance may be glyoxal.

Examples of the modifying resin may include a polyol resin, a phenol resin, an acrylic resin, a polyester resin, a polyolefin resin, an epoxy resin, and an epoxidized polybutadiene resin.

The coupling agent may improve adhesion and adhesion reliability between the adhesive composition and a packaging material. If the coupling agent is added, adhesion reliability may be improved in the case where a composition is maintained under high-temperature and/or high-humidity conditions for a long period of time. Examples of the coupling agent may include a silane compound such as γ-glycidoxypropyl triethoxy silane, γ-glycidoxypropyl trimethoxy silane, γ-glycidoxypropyl methyldiethoxy silane, γ-glycidoxypropyl triethoxy silane, 3-mercaptopropyl trimethoxy silane, vinyltrimethoxysilane, vinyltriethoxy silane, γ-methacryloxypropyl trimethoxy silane, γ-methacryloxy propyl triethoxy silane, γ-aminopropyl trimethoxy silane, γ-aminopropyl triethoxy silane, 3-isocyanato propyl triethoxy silane, γ-acetoacetatepropyl trimethoxysilane, γ-acetoacetatepropyl triethoxy silane, β-cyanoacetyl trimethoxy silane, β-cyanoacetyl triethoxy silane, and acetoxyaceto trimethoxy silane.

The kneading agent may be aromatic hydrocarbon resin.

The antiaging agent may be N-(1,3-dimethylbutyl)-N'-phenyl-p-phenylene diamine.

The wetting agent may be, for example, sugar, glycerin, a sorbitol aqueous solution, or an amorphous sorbitol aqueous solution, used alone or in combination.

The UV absorbent may be ethylhexyl methoxycinnamate (e.g., 2-ethylhexyl 4-methoxycinnamate), ethylhexylsalicylate, 4-methylbenzylidene camphor, isoamyl p-methoxycinnamate, octocrylene, phenylbenzimidazole sulfonic acid, homosalate, cynoxate, ethylhexyltriazone, polysilicone-15, TEA-salicylate, PABA, ethylhexyldimethyl PABA, glyceryl PABA, or the like. These compounds may be used alone or in combination of at least two.

The adhesive composition or adhesive product according to the present disclosure may further include additives disclosed in U.S. Pat. No. 4,959,412, CA1278132, U.S. Pat. No. 6,777,465, WO2007-120653, US2003-0064178, U.S. Pat. Nos. 7,306,844, 7,939,145, WO2011-136568, WO2010-071298, Korean Patent Application Publication No. 2016-0095132, Japanese Patent Application Publication No. 5959867, Korean Patent No. 989942, which are hereby incorporated by reference, in addition to the above-described additives.

The adhesive composition or adhesive product according to an embodiment may be used to attach labels or the like to various packing materials including metal, glass, and plastic. The packing materials may be, for example, containers for food, beverage, or household products, and these containers may be made of glass, metal, or plastic.

The adhesive composition or adhesive product may be used as adhesives, coating agents, carriers, food additives, or the like according to the composition and characteristics thereof.

When used as adhesives, the adhesive composition or adhesive product according to the present disclosure may be used as adhesives for labels, sealants, wallpaper, cigarette paper, adhesive block toys, sand sculpture, food, bath/kitchen detergents, animal ointment sprays, exfoliation, hair fixation, hair gel, soil stabilizers, water dispersion, strength agents on paper, corrugated board, zone adhesives, and the like. The soil stabilizers are used to remove fine dusts such as sandy dusts or dusts generated in factories.

When used as coating agents, the adhesive composition or adhesive product according to the present disclosure may be used for forest fire prevention, fruits and vegetables, truncated surfaces of flowers, dyes, antifouling pretreatment coating agents, and the like. In this case, the antifouling pretreatment coating agents may be coated on an easily contaminated medium and then contaminants may be simply removed therefrom by washing with water.

When used as carriers, the adhesive composition or adhesive product according to the present disclosure may be applied to forest protection against epidemics, forest fire prevention, air fresheners for bathrooms, disinfectants, agricultural materials, household products, toys, and the like. The forest protection against epidemics may be, for example, prevention of the spread of diseases such as pinewood nematode in forests. The disinfectants include, for example, avian influenza disinfectants and foot-and-mouth disease disinfectants. The agricultural materials may include fertilizers, taping materials, and seed coatings.

When used as agricultural materials, the adhesive composition or adhesive product according to the present disclosure may be applied to seed-coating agents, plant taping agents, insecticide additives, fertilizer excipients, natural pesticides, and the like. When used as household products, the adhesive composition according to the present disclosure may be added to paints to enhance adhesive forces thereof to paper without draining off or added to food colors to prepare edible paints used by toddlers. Another examples of household products, the adhesive composition may also be used as a decontamination pretreatment agent. Mores particularly, contaminants may be quickly removed by spraying the adhesive composition according to the present disclosure to contaminated media such as window screens, window frames, and automobiles and then washing the media with water.

When used as carriers, the adhesive composition or adhesive product according to the present disclosure may realize oxygen-blocking, moisture-blocking, oil-resistant, and heat-sealing functions. Thus, when used in coating layers of eco-friendly food packing materials, effects of preventing or delaying decay and oxidation of food may be obtained while inhibiting infiltration of external moisture. Also, when used as food additives, the adhesive composition or adhesive product according to the present disclosure may be applied to wheat gluten substitutes, jellys, starch syrups, cookies, food colors, ice creams, and antifreeze substances.

Hereinafter, one or more embodiments of the present disclosure will be described in detail with reference to the following examples. These examples are not intended to limit the purpose and scope of the one or more example embodiments of the present disclosure.

Example 1: Evaluation of Stability of Composition Including Lysine and Various Organic Acids Lysine, as basic amino acid, and various organic acids were mixed to prepare compositions. Stability of each composition (whether or not precipitates are formed) was evaluated.

Method of Preparing Adhesive Composition Including Lysine and Citric Acid:

79 g of distilled water (DIW) was added to 100 g of a 54 wt % aqueous solution of L-lysine free form while stirring the mixture at room temperature (25° C.) for 30 minutes to dilute lysine. 70.97 g of citric acid (CA) was slowly added to the diluted lysine at room temperature (25° C.) for 1 hour while stirring and then the mixture was further stirred at 60° C. for 1 hour. Then, the reaction mixture was cooled to room temperature (25° C.) to terminate the reaction and obtain 249.93 g of an adhesive composition. A solid content of this composition was about 50 parts by weight based on 100 parts by weight of the composition, a mixing molar ratio of lysine to citric acid was 1:1, and deionized water was used as a solvent.

Compositions were prepared in the same manner as described above by using different types of organic acids. The compositions were prepared in the same manner as in Example 1, except that organic acids shown in Table 1 below were used.

TABLE 1

| No. | Acid | Lysine:acid (mol ratio) | Solvent | Solid content (parts by weight) |
|---|---|---|---|---|
| 1-1 | Citric acid | 1:1 | DIW | 50 |
| 1-2 | Acetic acid | 1:1 | | |
| 1-3 | Glutamic acid | 1:1 | | |
| 1-4 | Glutaric acid | 1:1 | | |
| 1-5 | Tartaric acid | 1:1 | | |
| 1-6 | Aspartic acid | 1:1 | | |
| 1-7 | Fumaric acid | 1:1 | | |
| 1-8 | Glyoxylic acid | 1:1 | | |
| 1-9 | 4-ketopimelic acid | 1:1 | | |
| 1-10 | Pyruvic acid | 1:1 | | |
| 1-11 | 1,3-acetonedicarboxylic acid | 1:1 | | |

Formation of precipitates of the compositions prepared according to Table 1 was evaluated. Particularly, each of the compositions was applied to an OPP film (Sam Young Chemical Co., Ltd.) having a thickness of 50 μm by using a bar coater to a thickness of about 50 μm. After the film coated with the composition was maintained at room temperature (25° C.) at a relative humidity of 60±10% for 14 days, changes on the surface of the adhesive composition present on the OPP film were identified and evaluated. Evaluation results are shown in Table 2 below.

TABLE 2

| No. | Acid | Lysine:acid (mol ratio) | Solvent | Solid content (parts by weight) | State |
|---|---|---|---|---|---|
| 1-1 | Citric acid | 1:1 | DIW | 50 | Liquid state |
| 1-2 | Acetic acid | 1:1 | | | Precipitates |
| 1-3 | Glutamic acid | 1:1 | | | Precipitates |
| 1-4 | Glutaric acid | 1:1 | | | Precipitates |
| 1-5 | Tartaric acid | 1:1 | | | Precipitates |
| 1-6 | Aspartic acid | 1:1 | | | Precipitates |
| 1-7 | Fumaric acid | 1:1 | | | Precipitates |
| 1-8 | Glyoxylic acid | 1:1 | | | Precipitates |
| 1-9 | 4-ketopimelic acid | 1:1 | | | Precipitates |
| 1-10 | Pyruvic acid | 1:1 | | | Precipitates |
| 1-11 | 1,3-acetonedicarboxylic acid | 1:1 | | | Precipitates |

Referring to the results shown in Table 2, while precipitates were not formed in the composition including lysine and citric acid, precipitates were formed in the compositions including the other organic acids and lysine making evaluation of adhesion impossible. That is, in the case where compositions are prepared by mixing lysine and various organic acids, it was confirmed that not all of the compositions have adhesiveness without forming precipitates.

Example 2: Evaluation of Solubility According to Solvent of Composition

Adhesive compositions including lysine and citric acid were prepared in the same manner as in Example 1. 25 g of an additional solvent shown in Table 3 below was added 50 g of each of the prepared adhesive compositions (molar ratio of lysine to citric acid=1:1 and solid content: 50 parts by weight) and the mixture was stirred for 1 hour. After stirring, solubility of the adhesive composition to each solvent was identified. Types of the added solvent and evaluation results of solubility of the adhesive composition to each solvent are shown in Table 3 below.

TABLE 3

| No. | Added solvent | Solubility |
|---|---|---|
| 2-1 | Methanol | Dissolved |
| 2-2 | Toluene | Undissolved |
| 2-3 | Benzene | Undissolved |
| 2-4 | Chloroform | Undissolved |
| 2-5 | Methylenechloride | Undissolved |
| 2-6 | Dichloromethane | Undissolved |
| 2-7 | Tetrahydrofuran (THF) | Undissolved |
| 2-8 | Ethyl acetate | Undissolved |
| 2-9 | Dimethylformamide(DMF) | Undissolved |
| 2-10 | Dimethylsulfoxide (DMSO) | Undissolved |
| 2-11 | n-hexane | Undissolved |

Referring to Table 3, the adhesive composition according to the present disclosure was dissolved in an alcohol such as methanol used as a solvent, but not dissolved in the other organic solvents.

Example 3: Analysis of State, Viscosity, and Initial Tack of Adhesive Composition According to Mixing Molar Ratio of Lysine to Citric Acid Stability, viscosity, and initial tack of adhesive compositions of the present disclosure according to the molar ratio of lysine to citric acid included in the adhesive compositions were analyzed.

Adhesive compositions including lysine and citric acid were prepared in the same manner as in Example 1 by adjusting molar ratios of lysine to citric acid to 3:1. 2.5:1, 2:1, 1.5:1, 1:1, 1:1.5, 1:2, 1:2.5, and 1:3, respectively (solid content: 50 parts by weight).

(1) Evaluation of Stability

Stability of the adhesive compositions having various molar ratios was evaluated according to the following method. About 1 g of each of the adhesive compositions was applied to an aluminum dish having a diameter of 5 cm. Then, formation of precipitates was identified in the adhesive composition under the following drying conditions.

i) Drying Conditions 1

The adhesive compositions were maintained at room temperature (25° C.) at a relative humidity of 60±10% for 14 days to identify formation of precipitates and changes on the surfaces thereof.

ii) Drying Conditions 2

The adhesive composition were maintained in an oven at 40° C. for 48 hours to identify formation of precipitates and changes on the surfaces thereof.

(2) Evaluation of Viscosity

Viscosity was measured using a rotary viscometer (Manufacturer: LAMYRHEOLOGY, Product Name: RM200 TOUCH CP400 or RM200 TOUCH) at 25±1° C. using a LV-1 spindle at 60 rpm.

(3) Evaluation of Initial Tack

Initial tacks of the adhesive compositions in which precipitates were not formed in the evaluation of stability were evaluated. Initial tacks of the adhesive compositions were measured by a rheometer of Anton Paar, Co., Ltd and compared using the rheometer. A SUS probe having a diameter of 25 mm was brought into contact with each adhesive composition for 1 minute to maintain a gap of 0.01 mm, and then a force generated to separate the probe at the same speed was measured to quantitatively evaluate an instantaneous initial tack.

Evaluation results are shown in Table 4 below.

TABLE 4

Figure 3:
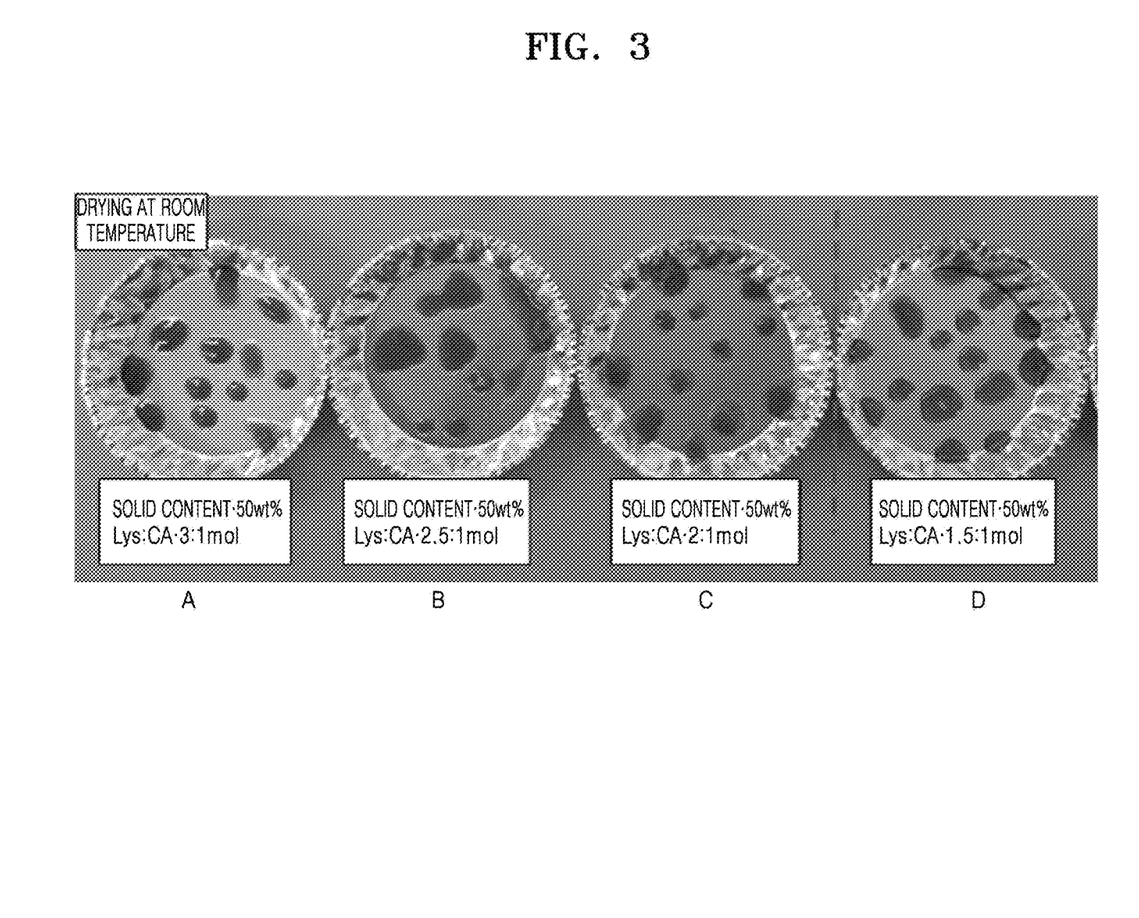
FIG. 3 shows a photograph of adhesive compositions applied to substrates and dried at room temperature (25° C.), according to Example 3.
Figure 4:
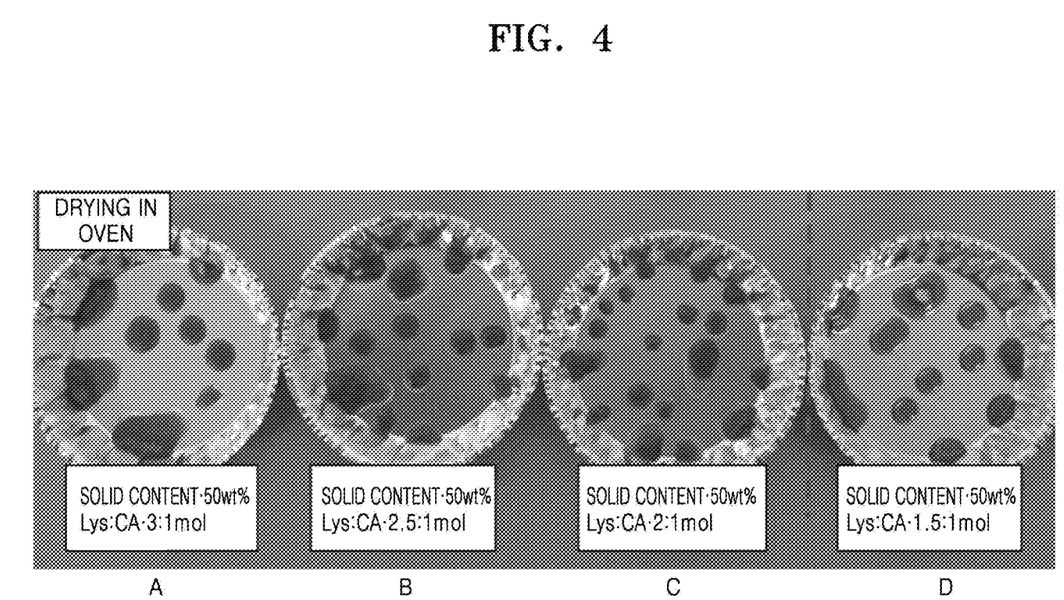
FIG. 4 shows photographs of adhesive compositions applied to substrates and dried in an oven (40° C.), according to Example 3.

| No. | Lysine:CA (mol ratio) | Solid content (parts by weight) | Viscosity (mPa · s) | Initial tack (mJ) | State | Note |
|---|---|---|---|---|---|---|
| 3-1 | 3:1 | 50 | 40.77 | — | Precipitates | Room temperature: A of FIG. 3 Oven: A of FIG. 4 |
| 3-2 | 2.5:1 |  | 36.54 | — | Precipitates | Room temperature: B of FIG. 3 Oven: B of FIG. 4 |
| 3-3 | 2:1 |  | 32.53 | — | Precipitates | Room temperature: C of FIG. 3 Oven: C of FIG. 4 |
| 3-4 | 1.5:1 |  | 28.84 | 0.245 | Liquid state | Room temperature: D of FIG. 3 Oven: D of FIG. 4 |
| 3-5 | 1:1 |  | 26.68 | 0.222 | Liquid state |  |
| 3-6 | 1:1.5 |  | 25.76 | 0.22 | Liquid state |  |
| 3-7 | 1:2 |  | 23.31 | 0.215 | Liquid state |  |
| 3-8 | 1:2.5 |  | 22.15 | 0.213 | Liquid state |  |
| 3-9 | 1:3 |  | 20.12 | 0.212 | Liquid state |  |

*In Table 4, room temperature refers to drying conditions 1 and oven refers to drying conditions 2.

Referring to Table 4, precipitates were formed in the adhesive compositions in which the molar ratio of lysine to citric acid was in the range of 3:1 to 2:1.

While precipitates were formed in the adhesive composition in which the molar ratio of lysine to citric acid was 2:1, precipitates were not formed at a molar ratio of lysine to citric acid of 1.5:1. In order to identify a more specific critical point, adhesive compositions were prepared by subdividing the molar ratio of lysine to citric acid into 2:1, 1.9:1, 1.8:1, 1.7:1, 1.6:1, and 1.5:1 (where the solid content was 50 parts by weight). Then, stability, viscosity, and initial tack thereof were evaluated in the same manner.

Evaluation results are shown in Table 5 below.

TABLE 5

| No. | Lysine:CA (mol ratio) | Solid content (wt %) | Viscosity (mPa · s) | Initial tack (mJ) | State |
|---|---|---|---|---|---|
| 3-10 | 2:1 | 50 | 32.53 | — | Precipitates |
| 3-11 | 1.9:1 |  | 31.76 | — | Precipitates |
| 3-12 | 1.8:1 |  | 30.11 | — | Precipitates |
| 3-13 | 1.7:1 |  | 29.45 | 0.255 | Liquid state |
| 3-14 | 1.6:1 |  | 28.90 | 0.249 | Liquid state |
| 3-15 | 1.5:1 |  | 28.84 | 0.245 | Liquid state |

Referring to Table 5, while precipitates were formed at a molar ratio of lysine to citric acid of 2:1 to 1.8:1, precipitates were not formed at a molar ratio of lysine to citric acid of 1.7:1 to 1.5:1.

Example 4: Analysis of State, Viscosity, and Initial Tack of Adhesive Composition According to Solid Content State, viscosity, and initial tack of the adhesive compositions of the present disclosure according to the solid content were analyzed.

1) Evaluation According to Solid Content at a Molar Ratio of Lysine to Citric Acid of 1:1

Adhesive compositions including lysine and citric acid were prepared in the same manner as in Example 1, except that solid contents in the adhesive compositions were adjusted to 10 wt %, 20 wt %, 30 wt %, 40 wt %, 50 wt %, 60 wt %, 70 wt %, and 75 wt % respectively (where the molar ratio of lysine to citric acid was 1:1). Here, the solid content was adjusted by using water.

States, viscosity, and initial tack of the compositions were evaluated in the same manner as in Example 3. Evaluation results are shown in Table 6 below.

TABLE 6

| No. | Lysine:CA (mol ratio) | Solid content (wt %) | Viscosity (mPa · s) | Initial tack (mJ) | State |
|---|---|---|---|---|---|
| 4-1 | 1:1 | 10 | 10.08 | 0.21 | Liquid state |
| 4-2 | 1:1 | 20 | 11.84 | 0.217 | Liquid state |
| 4-3 | 1:1 | 30 | 13.54 | 0.216 | Liquid state |
| 4-4 | 1:1 | 40 | 16.24 | 0.22 | Liquid state |
| 4-5 | 1:1 | 50 | 26.68 | 0.222 | Liquid state |
| 4-6 | 1:1 | 60 | 85.28 | 0.523 | Liquid state |
| 4-7 | 1:1 | 70 | 657.67 | 1.48 | Liquid state |
| 4-8 | 1:1 | 75 | Insoluble material (CA) | | |

Referring to Table 6, it was confirmed that the solid content are not dissolved in the adhesive composition and precipitates were formed when the solid content in the compositions was 75 wt %.

While precipitates were formed when the solid content in the compositions was 75 wt %, precipitates were not formed when the solid contents in the compositions were 60 wt % and 70 wt %. In order to identify a more specific critical point, adhesive compositions were prepared by subdividing the solid content into 60 wt %, 61 wt %, 62 wt %, 63 wt %, 64 wt %, 65 wt %, 66 wt %, 67 wt %, 68 wt %, 69 wt %, 70 wt %, 71 wt %, and 72 wt % in the compositions (where the molar ratio of lysine to citric acid was 1:1). Then, stability, viscosity, and initial tack thereof were evaluated in the same manner.

Evaluation results are shown in Table 7 below.

TABLE 7

| No. | Lysine:CA (mol ratio) | Solid content (wt %) | Viscosity (mPa · s) | Initial tack (mJ) | State |
|---|---|---|---|---|---|
| 4-9 | 1:1 | 60 | 85.28 | 0.523 | Liquid state |
| 4-10 | 1:1 | 61 | 91.45 | 0.562 | Liquid state |
| 4-11 | 1:1 | 62 | 99.13 | 0.614 | Liquid state |
| 4-12 | 1:1 | 63 | 115.22 | 0.652 | Liquid state |
| 4-13 | 1:1 | 64 | 125.35 | 0.751 | Liquid state |
| 4-14 | 1:1 | 65 | 168.5 | 0.783 | Liquid state |
| 4-15 | 1:1 | 66 | 184.15 | 0.899 | Liquid state |
| 4-16 | 1:1 | 67 | 233.56 | 0.921 | Liquid state |
| 4-17 | 1:1 | 68 | 290.52 | 1.12 | Liquid state |
| 4-18 | 1:1 | 69 | 424.2 | 1.24 | Liquid state |
| 4-19 | 1:1 | 70 | 657.67 | 1.48 | Liquid state |
| 4-20 | 1:1 | 71 | Insoluble material (CA) | | |
| 4-21 | 1:1 | 72 | Insoluble material (CA) | | |

Referring to Table 7, while the adhesive compositions were maintained in liquid states when the solid content was 70 wt % in the adhesive composition, precipitates were formed within two weeks when the solid content was 71 wt % or greater in the adhesive composition.

2) Evaluation According to Solid Content at a Molar Ratio of Lysine to Citric Acid of 1:2, 1:3, or 2:1

Formation of precipitates according to the solid content was evaluated while the molar ratio of lysine to citric acid varies.

Adhesive compositions including lysine and citric acid were prepared in the same manner as in Example 1, except that the molar ratios of lysine to citric acid were adjusted to 1:2, 1:3, and 2:1, respectively. The content of water was adjusted such that the solid contents of the compositions were adjusted to 10 wt %, 20 wt %, 30 wt %, 40 wt %, 50 wt %, 60 wt %, 70 wt % respectively. Stability of the compositions were evaluated in the same manner as in Example 1. Evaluation results are shown in Table 8 below.

TABLE 8

| No. | Lysine:CA (mol ratio) | Solid content (wt %) | State |
|---|---|---|---|
| 4-22 | 1:2 | 10 | Liquid state |
| 4-23 | | 20 | Liquid state |
| 4-24 | | 30 | Liquid state |
| 4-25 | | 40 | Liquid state |
| 4-26 | | 50 | Liquid state |
| 4-27 | | 60 | Liquid state |
| 4-28 | | 70 | Liquid state |
| 4-29 | 1:3 | 10 | Liquid state |
| 4-30 | | 20 | Liquid state |
| 4-31 | | 30 | Liquid state |
| 4-32 | | 40 | Liquid state |
| 4-33 | | 50 | Liquid state |
| 4-34 | | 60 | Liquid state |
| 4-35 | | 70 | Liquid state |
| 4-36 | 2:1 | 10 | Precipitates |
| 4-37 | | 20 | Precipitates |
| 4-38 | | 30 | Precipitates |
| 4-39 | | 40 | Precipitates |
| 4-40 | | 50 | Precipitates |

Referring to Table 8, precipitates were not formed at molar ratios of lysine to citric acid of 1:2 and 1:3 although the solid contents vary from 10 wt % to 70 wt %. However, precipitates were formed when the molar ratio of lysine to citric acid was 2:1 regardless of the sold content.

That is, it may be confirmed that the molar ratio of lysine to citric acid is the most important factor affecting stability and adhesive force of the adhesive composition according to the present disclosure. At the same molar ratio of the lysine to citric acid, stability and adhesive force of the adhesive composition is affected by the solid content.

Example 5: Comparison of Initial Tack and Water Removability

Adhesive forces and water removability were compared between a conventional adhesive and the adhesive composition according to the present disclosure.

Adhesive compositions including lysine and citric acid were prepared in the same manner as in Example 1, except that the solid content was adjusted to 10 wt % in the adhesive compositions by adjusting the content of water (where the molar ratio of lysine to citric acid was 1:1)

A commercially available polyvinyl alcohol-based adhesive (PVA 088-50, Qingdao Sanhuan Colorchem CO., LTD.) was prepared and the solid content was adjusted to 10 wt % by controlling the content of water (hereinafter, referred to as Control 1).

Viscosity and initial tack of the adhesive compositions according to the present disclosure (solid content: 10 wt %) and Control 1 were evaluated in the same manner as in Example 3.

Water removability of the adhesive compositions according to the present disclosure (solid content 10 wt %) and Control 1 was evaluated. Water removability was evaluated according to the following method. The adhesive composition according to the present disclosure was applied to a PET film to a thickness of 50 to 60 μm and dried at 40° C. for 30 minutes. A dried resultant was cut to a size of 25 mm×25 mm and attached to a stainless steel (SUS304) by pressing five times at a pressure of 2 kgf by using a hand roller to prepare a sample. A PVA adhesive was applied to a PET film to a thickness of 50 to 60 μm, cut to a size of 25 mm×25 mm, attached to a stainless steel (SUS304) by pressing five times at a pressure of 2 kgf by using a hand roller to prepare a sample.

Each of the samples was completely immersed in distilled water (DIW) at room temperature, atmospheric pressure, and a neutral pH and stirred at 200 rpm by using a stirrer. States of the samples were identified i) after 1 hour or ii) after 24 hours. Then, periods of time during which the samples according to the present disclosure and the adhesive of Control 1 were completely removed were measured to evaluate water removability of the samples.

Evaluation results are shown in Table 9 below.

TABLE 9

| | Solid content (wt %) | Viscosity (mPa · s) | Initial tack (mJ) | Water removability |
|---|---|---|---|---|
| 5-1 | 10 | 10.1 | 0.21 | Separated within 1 hour |
| Control 1 (PVA-based) | 10 | 43.49 | 0.201 | i) partially dissolved in water after 1 hour or ii) dissolved in water after 24 hours, at 200 rpm. |

Referring to Table 9, the adhesive composition according to the present disclosure exhibited a similar initial tack and was quickly separated in water in comparison with the PVA-based adhesive composition (Control 1). On the contrary, the PVA-based adhesive composition was dissolved in water after 24 hours but partially dissolved in water after 1 hour.

That is, the adhesive composition according to the present disclosure has a similar or better adhesive force and far better water removability than conventional adhesives, and thus it is expected to utilize the adhesive composition according to the present disclosure in various fields.

Example 6: Evaluation of Peel Strength and Water Removability According to Solvent Adhesive compositions including lysine and citric acid were prepared in the same manner as in Example 1 (6-1 to 6-3 below), except that the molar ratios of lysine to citric acid were adjusted to 1.5:1, 1:1, and 1:1.5 (where the solid content was 50 parts by weight)

Adhesive compositions including lysine and citric acid were further prepared in the same manner as in Example 1 (6-4 to 6-6 below), except that molar ratios of lysine to citric acid were adjusted to 1.5:1, 1:1, and 1:1.5, and methanol was further added thereto as a solvent. Here, a weight ratio of deionized water to methanol was 1:1 (where the solid content was 50 parts by weight).

Additionally, adhesive compositions including lysine and citric acid were prepared in the same manner as in Example 1 (6-7 to 6-8 below), except that methanol was further added thereto in addition to deionized water and weight ratios of deionized water to methanol were 6:4 and 4:6. (where the molar ratio of lysine to citric acid was 1:1, and the solid content was 50 parts by weight).

As a control, a commercially available acrylic adhesive (K901, Hansung P&I, hereinafter, referred to as Control 2, where the solid content was 59 wt %) was prepared. Peel strength and water removability of the adhesive compositions were evaluated according to the following methods, and evaluation results are shown in Table 10 below.

1) Peel Strength

PET films were prepared (film standards: 120 mm×25 mm and thicknesses: 38 μm or 50 μm), and a sample was coated to a surface of the PET film (having a thickness of 50 μm) to a thickness of 11 μm by using a bar coater. Then, the PET film was dried in an oven at 60° C. for 4 minutes and then laminated on a PET film (having a thickness of 38 μm) by using a dry laminator (at a roller speed of 1.9 m/min and a roller temp. of 60° C.). The laminated sample was dried in an oven at 30° C. for 72 hours. Peel strength of the dried sample was measured in accordance with the ASTM D1876 "180° T peel strength measurement" method.

2) Water Removability

The prepared adhesive compositions according to the present disclosure and Control 2 were applied to the PET film to a thickness of 50 to 60 μm and dried at 40° C. for 30 minutes.

Dried resultants were cut to a size of 25 mm×25 mm and attached to a stainless steel (SUS304) by pressing five times at a pressure of 2 kgf by using a hand roller to prepare samples.

Each of the samples was completely immersed in distilled water (DIW) at room temperature, atmospheric pressure, and a neutral pH and stirred at 200 rpm by using a stirrer. States of the samples were identified i) after 1 hour or ii) after 24 hours

TABLE 10

| No. | Lysine:CA (mol ratio) | Solvent | Solid content (parts by weight) | Peel strength (N/25 mm) | Water removability |
|---|---|---|---|---|---|
| 6-1 | 1.5:1 | DIW | 50 | 5.91 | Completely dissolved in water |
| 6-2 | 1:1 | | | 5.45 | |
| 6-3 | 1:1.5 | | | 4.92 | |
| 6-4 | 1.5:1 | DIW and methanol (1:1 in weight) | | 7.11 | i) after 1 hour or ii) after 24 hours, at 200 rpm. |
| 6-5 | 1:1 | | | 6.92 | |
| 6-6 | 1:1.5 | | | 6.18 | |
| 6-7 | 1:1 | DIW and methanol (6:4 in weight) | | 6.28 | |
| 6-8 | 1:1 | DIW and methanol (4:6 in weight) | | — | Phase separation |
| Control 2 (acrylic) | — | | 59 | 6.61 | Undissolved in water |

Referring to Table 10, an adhesive product obtained by using the adhesive composition according to the present disclosure was separated within 1 hour after being immersed in water. In addition, it was confirmed that peel strength was further increased when the alcohol solvent is further used together with water. These results may be obtained because the adhesive composition including a mixed solvent has a lower contact angle than that including only deionized water and better coating properties on a substrate film. However, when a weight ratio of deionized water to alcohol was 4:6, phase separation occurred in the adhesive composition. Although the adhesive composition according to the present disclosure exhibited similar peel strength even with a lower solid content in comparison with the conventional acrylic adhesive (Control 2). However, the acrylic adhesive was not dissolved in water even after 25 hours.

Example 7: Composition Analysis of Adhesive Composition According to Reaction Temperature Composition of adhesive compositions according to reaction temperature were analyzed.

1) Preparation at 0° C. (low temperature): 79 g of DIW was added to 100 g of a 54 wt % aqueous solution of lysine and the mixture was stirred at 0° C. (T1) for 30 minutes. The diluted resultant was stirred while adding 70.97 g of citric acid thereto at 0° C. (T2) for 1.5 hours to prepare an adhesive composition (solid content: 50 wt % and mixing ratio of lysine to citric acid=1:1). An ice bath was used to maintain the same temperature of the adhesive composition while stirring.

2) Preparation at 25° C. (room temperature): 79 g of DIW was added to 100 g of a 54 wt % aqueous solution of lysine and the mixture was stirred at room temperature (T1) for 30 minutes. The diluted resultant was stirred while adding 70.97 g of citric acid thereto at 25° C. (T2) for 1.5 hours to prepare an adhesive composition (solid content: 50 wt % and mixing ratio of lysine to citric acid=1:1). A temperature controller was used to maintain the same temperature while stirring (The same method is used in the following cases).

3) Preparation at 60° C.: An adhesive composition was prepared in the same manner as in the above method 2), except that T2 was changed to 60° C.

4) Preparation at 80° C.: An adhesive composition was prepared in the same manner as in the above method 2), except that T2 was changed to 80° C.

5) Preparation at 240° C.: An adhesive composition was prepared in the same manner as in the above method 2), except that T2 was changed to 240° C.

As a result of preparing the compositions as described above, carbide was formed at 240° C., making it impossible to produce an adhesive composition. Thus, composition analysis was performed on the compositions prepared at 0° C., 25° C., 60° C., and 80° C. using $^1$H NMR.

An NMR spectrometer and analysis conditions used in the present disclosure are as follows.

Superconducting Fourier transform nuclear magnetic resonance spectrometer (400 MHz) (Model No.: AVANCE II 400, Manufacturer: Bruker Biospin (Magnet field strength 9.4 Tesla, Field drift rate: 4 Hz/hr, Observable Frequency: 400 Mhz 1H, Sensitivity: 220:1(1H), Variable Temp.: −70 to +110° C.), and solvent: $D_2O$)

Figure 1:
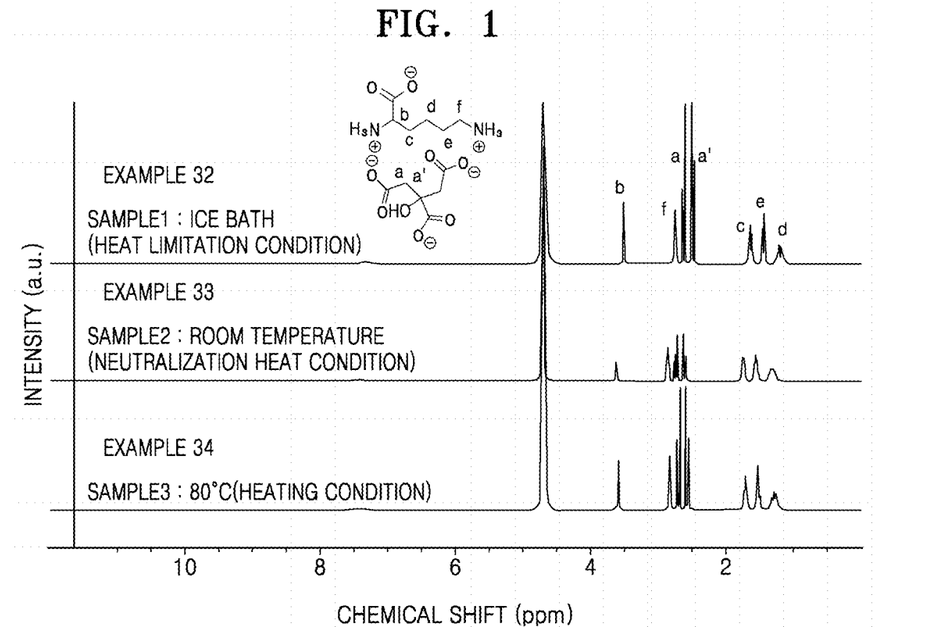
FIG. 1 is a graph illustrating $^1$H nuclear magnetic resonance (NMR) analysis results, according to Example 7.

The compositions prepared at 0° C., 25° C., and 80° C. were analyzed by using $^1$H NMR. NMR analysis results are shown in FIG. 1. Referring to FIG. 1, $^1$H NMR peaks were observed at the same position in the compositions prepared at 0° C., 25° C., and 80° C., and no chemical shift was observed. Thus, it was confirmed that the compositions had the same composition. That is, lysine and citric acid are present in a mixed state and no condensate, or very little condensate, of lysine and citric acid was generated in the adhesive compositions prepared at 0° C., 25° C., and 80° C.

Example 8: Composition Analysis of Adhesive Composition According to Reaction Time Composition ratios of adhesive compositions according to reaction time were analyzed.

1) Preparation at 60° C.: 7.56 g of DIW was added to 100 g of a 54 wt % aqueous solution of lysine and the mixture was stirred at 25° C. (T1) for 30 minutes. The diluted resultant was stirred while slowly adding 70.97 g of citric acid thereto at 60° C. (T2) for 9 hours to prepare an adhesive composition (solid content: 70 wt % and mixing ratio of lysine to citric acid=1:1). Composition analysis was performed on the adhesive composition at every 3 hours.

2) Preparation at 80° C.: An adhesive composition was prepared in the same manner as in the above method 1), except that T2 was changed to 80° C. Composition analysis was performed on the adhesive composition at every 3 hours.

Composition analysis was performed on the prepared compositions by HPLC.

Analysis results are shown in Table 1 below.

TABLE 11

| Temperature | Reaction time (hr) | Amount of Lysine (wt %) | Amount of Citric acid (wt %) |
| --- | --- | --- | --- |
| 80° C. | 0 | 38.34 | 29.83 |
|  | 3 | 37.33 | 28.93 |
|  | 6 | 36.29 | 28.17 |
|  | 9 | 35.22 | 26.97 |
| 60° C. | 0 | 39.43 | 30.24 |
|  | 3 | 39.04 | 30.14 |
|  | 6 | 39.71 | 30.28 |
|  | 9 | 39.15 | 30.01 |
|  | 12 | 38.49 | 29.94 |

Referring to Table 11, after addition of citric acid, the weights of lysine and citric acid were maintained at the almost same levels (within experimental error) in the adhesive composition prepared by stirring at 60° C. However, after addition of citric acid, the amounts of lysine and citric acid were slightly reduced in the adhesive composition prepared by stirring at 80° C. Thus, it may be estimated that a small amount of a condensate of lysine and citric acid was generated. As a result of analyzing the other substances except for lysine and citric acid, the amount of the condensate was less than 10 wt % based on a total of initial weights of lysine and citric acid.

Example 9: Evaluation of Contact Angle of Substrate with Adhesive Composition

Contact angles of the adhesive compositions with substrates were measured by using a contact angle meter (Product name: phoenix, measurement conditions: drop volume 5 μl). Contact angles may be measured by dropping a predetermined amount of a liquid by using a micro pipet or a syringe and measuring an angle of a droplet via software. In general, a lower contact angle may be evaluated as a better adhesive.

Adhesive compositions including lysine and citric acid were prepared in the same manner as in Example 1, except that the solid contents were adjusted to 10 wt %, 20 wt % and 30 wt % in the adhesive compositions, respectively (where the molar ratio of lysine to citric acid was 1:1). The solid content was adjusted by controlling the amount of water.

Contact angles of the adhesive compositions according to the present disclosure were evaluated using glass, SUS, and PE as substrates. In a control, diiodomethane and distilled water were used.

Figure 2:
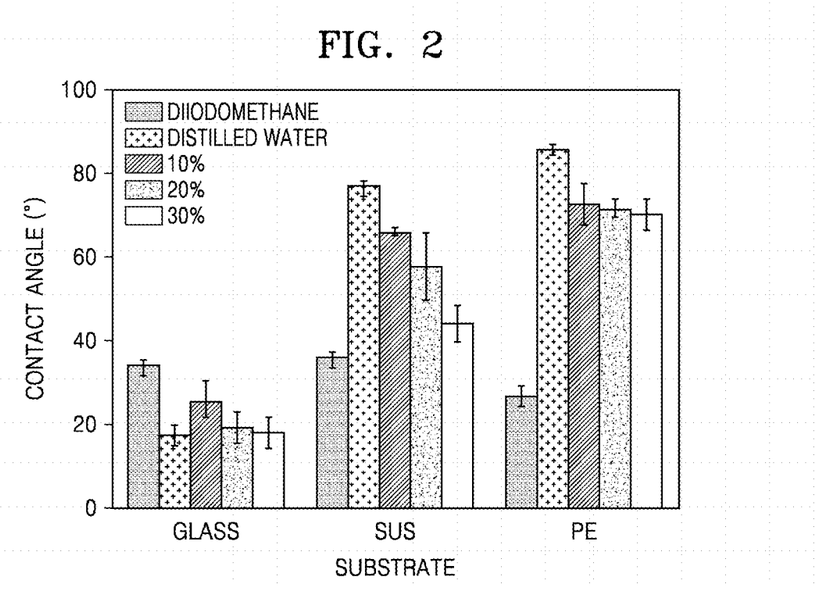
FIG. 2 is a graph illustrating evaluation results of contact angles with glass, stainless steel (SUS), and polyethylene (PE) substrates, according to Example 10.

Contact angle measurement results are shown in FIG. 2.

Referring to FIG. 2, since a glass substrate is a hydrophilic substrate, diiodomethane that is a non-polar compound had a relatively high contact angle with the glass substrate and distilled water had a relatively low contact angle therewith. Since the adhesive composition having the solid content of 10 parts by weight is applied thereto, polarity decreases and thus a contact angle thereof with the substrate increases. However, the contact angle of the adhesive composition decreased as the solid content increased in the adhesive composition that is a hydrophilic substance.

When an SUS substrate was used, citric acid included in the adhesive composition induces interactions with SUS. Thus, as the solid content increases in the adhesive composition, the contact angle decreases with the SUS substrate. In addition, a PE substrate is hydrophobic. Thus, when the non-polar diiodomethane is applied to the PE substrate, a contact angle of diiodomethane with the PE substrate is relatively low and a contact angle of distilled water is relatively high. Since polarity of distilled water decreases by adding the adhesive composition, the contact angle was slightly decreased. As a result, it was confirmed that the contact angle of the adhesive composition with a substrate decreases when the adhesive composition according to the present disclosure is applied to a hydrophilic substrate or a substrate having a high surface energy.

As described above, the adhesive composition according to the present disclosure may be used as a water-removable adhesive, a coating agent, and a carrier. When used as the water-removable adhesive, the adhesive composition may be easily removed from an adherend or a substrate by water. Thus, the adhesive is echo-friendly due to water removability.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the inventive concept as defined by the following claims.

What is claimed is:

1. An adhesive composition comprising lysine, citric acid, and water,
    wherein the lysine and the citric acid are present in the form of an aqueous solution of a salt and do not form precipitates in the aqueous solution,
    wherein a mixing molar ratio of the lysine to the citric acid is adjusted such that precipitates of the lysine and the citric acid are not formed in the adhesive composition, and
    wherein the mixing molar ratio of the lysine to the citric acid is from 1.7:1 to 1:3.

2. The adhesive composition of claim 1, wherein the precipitates are precipitates of the lysine and the citric acid.

3. The adhesive composition of claim 1, wherein a solid content of the adhesive composition is equal to or less than 70 parts by weight based on a total weight of the adhesive composition.

4. The adhesive composition of claim 1, further comprising at least one solvent selected from a primary alcohol, a polyhydric alcohol, a diol, and a triol.

5. The adhesive composition of claim 4, wherein the solvent comprises: at least one monohydric alcohol selected from methanol, ethanol, propane-2-ol, butane-1-ol, pentane-1-ol, and hexadecane-1-ol; at least one polyhydric alcohol selected from ethane-1,2-diol, propane-1,2-diol, propane-1,2,3-triol, butane-1,3-diol, butane-1,2,3,4-tetraol, pentane-1,2,3,4,5-pentol, hexane-1,2,3,4,5,6-hexol, and heptane-1,2,3,4,5,6,7-heptol; at least one unsaturated aliphatic alcohol selected from prop-2-ene-1-ol, 3,7-dimethylocta-2,6-dien-1-ol, and prop-2-yn-1-ol; at least one alicyclic alcohol selected from cyclohexane-1,2,3,4,5,6-hexol and 2-(2-propyl)-5-methylcyclohexane-1-ol; or a mixture thereof.

6. The adhesive composition of claim 1, wherein precipitates are not formed in the adhesive composition when stored at a temperature of −18° C. to 45° C. for 14 days or longer.

7. The adhesive composition of claim 1, wherein a contact angle of the adhesive composition with a surface of a substrate to which the adhesive composition is applied is from 15° to 70°.

8. A method of preparing an adhesive composition, the method comprising:
    mixing lysine, citric acid, and water to thereby form a mixture of the lysine, the citric acid, and the water; and
    stirring the mixture at a temperature of 80° C. or less,
    wherein amounts of the lysine, the citric acid, and the water are adjusted such that precipitates of the lysine and the citric acid are not formed in the adhesive composition, wherein the mixing molar ratio of the lysine to the citric acid is from 1.7:1 to 1.3.

9. The method of claim 8, wherein the mixture further comprises at least one solvent selected from a primary alcohol, a polyhydric alcohol, a diol, and a triol.

10. An adhesive product comprising the adhesive composition of claim 1.

* * * * *